United States Patent [19]
Krammer et al.

[11] Patent Number: 5,891,434
[45] Date of Patent: Apr. 6, 1999

[54] MONOCLONAL ANTIBODIES TO THE APO-1 ANTIGEN

[75] Inventors: Peter H. Krammer; Klaus-Michael Debatin, both of Heidelberg; Bernhard C. Trauth, Mannheim; Iris Behrmann, Heidelberg; Jens Dhein, Edingen-Nhsn; Christiane Klas, Lörrach; Peter Möller, Heidelberg; Werner Falk, Schönhofen/Nittendorf; Alexander Oehm, Wiesbaden; Peter T. Daniel, Reutlingen, all of Germany

[73] Assignee: Centocor, Inc., Malvern, Pa.

[21] Appl. No.: 409,338

[22] Filed: Mar. 23, 1995

Related U.S. Application Data

[63] Continuation of Ser. No. 260,644, Jun. 16, 1994, abandoned, which is a continuation-in-part of Ser. No. 691,016, filed as PCT/EP90/00111 Jan. 19, 1990 published as WO91/10448, Jul. 25, 1991, abandoned.

[51] Int. Cl.$^6$ .................. A61K 39/395; A61K 39/00; C12P 21/04; C07K 16/00

[52] U.S. Cl. .................. 424/143.1; 435/70.21; 435/172.2; 435/240.27; 434/152.1; 434/153.1; 434/154.1; 434/155.1; 434/156.1; 434/172.1; 434/173.1; 434/174.1; 434/277.1; 530/387.1; 530/387.3; 530/388.75; 530/388.8; 530/388.85; 530/389.7

[58] Field of Search .................. 424/152.1, 153.1, 424/154.1, 155.1, 156.1, 172.1, 173.1, 174.1, 277.1, 143.1; 530/387.1, 383.3, 388.75, 388.8, 388.85, 389.7; 435/70.21, 172.2, 240.27

[56] References Cited

FOREIGN PATENT DOCUMENTS

0311438A2 12/1989 European Pat. Off. .
90/00111 9/1990 WIPO .

OTHER PUBLICATIONS

Trauth, Bernhard C. et al., "Monoclonal Antibody–Mediated Tumor Regression by Induction of Apoptosis," *Science* 245:301–305 (1989).
Smith, Christopher A. et al., "Antibodies to CD3/T–cell receptor complex induce death by apoptosis in immature T cells in thymic cultures," *Nature* 337:181–184 (1989).
Blackman, Marcia et al., "The Role of the T Cell Receptor in Positive and Negative Selection of Developing T Cells," *Science* 248:1335–1341 (1990).
Acuto, Oreste et al., "The Human T Cell Receptor: Appearance in Ontogeny and Biochemical Relationship of α and β Subunits on IL–2 Dependent Clones and T Cell Tumors," *Cell* 34:717–726 (1993).
Schwarting, R. et al., "Immunoprecipitation of the Interleukin–2 Receptor from Hodgkin's Disease Derived Cell Lines by Monoclonal Antibodies," *Hematological Oncology* 5(1):57–64 (1987).
Takahashi, Shuji et al., "DNA fragmentation and cell death mediated by T cell antigen receptor/CD3 complex on a leukemia T cell line," *Eur. J. Immunol.* 19:1911–1919 (1989).
Osband et al., "Problems In The Investigational Study And Clinical Use of Cancer Immunotherapy", *Immunology Today* 11(6):193–195, 1990.
Waldman, T.A., "Monoclonal Antibodies In Diagnosis And Therapy", *Science* 252: 1657–1662, 21 Jun. 1991.

(List continued on next page.)

*Primary Examiner*—Jeffrey Stucker
*Assistant Examiner*—Hankyel T. Park
*Attorney, Agent, or Firm*—Hamilton, Brook, Smith & Reynolds, P.C.

[57] ABSTRACT

The APO-1 cellular membrane antigen, an about 50 kDa antigen associated with cellular apoptosis, and purified cDNA encoding same is described. The antigen is expressed by numerous normal and malignant cells, including activated and malignant lymphoid cells. Also disclosed are antibodies which bind the antigen, and which induce growth inhibition and apoptosis.

11 Claims, 1 Drawing Sheet

```
                                                                            *
  1 MLGIWTLLPL VLTSVARLSS KSVNAQVTDI NSKGLELRKT VTTVETQNLE GLHHDGQFCH  60
        *           *        *  *                  * * *              *
 61 KPCPPGERKA RDCTVNGDEP DCVPCQEGKE YTDKAHFSSK CRRCRLCDEG HGLEVEINCT 120
         * *        *    *   * * *              *          *         *
121 RTQNTKCRCK PNFFCNSTVC EHCDPCTKCE HGIIKECTLT SNTKCKEEGS RSNLGWLCLL 180
                            *
181 LLPIPLIVWV KRKEVQKTCR KHRKENQGSH ESPTLNPETV AINLSDVDLS KYITTIAGVM 240

241 TLSQVKGFVR KNGVNEAKID EIKNDNVQDT AEQKVQLLRN WHQLHGKKEA YDTLIKDLKK 300
        *
301 ANLCTLAEKI QTIILKDITS DSENSNFRNE IQSLV 335
```

OTHER PUBLICATIONS

Dillman, R.O., "Monoclonal Antibodies For Treating Cancer", *Annals Int. Medicine* 111:592–603, 1989.

Hird et al, "Immunotherapy With Monoclonal Antibodies", in *Genes and Cancer,* Carney et al., Eds., Wiley and Sons Ltd., 1990.

Trauth et al., "Monoclonal Antibody–Mediated Tumor Regression By Induction of Apoptosis," *Science* 245:301–305, 21 Jul. 1989.

Yonchara et al., "A Cell–Killing Monoclonal Antibody (Anti–Fas) To A Cell Surface Antigen Co–Downregulation With The Receptor Of Tumor–Necrosis Factor," *J. Exp. Med.* 169:1747–1756, May 1989.

Marx, J., "Cell Death Studies Yield Cancer Clues," *Science,* 259:760–761, 5 Feb. 1993.

Cohen, J.J., "Apoptosis," *Immunology Today* 14(3):126–130, 1993.

```
  1 MLGIWTLLPL VLTSVARLSS KSVNAQVTDI NSKGLELRKT VTTVETQNLE GLHHDGQFCH  60
 61 KPCPPGERKA RDCTVNGDEP DCVPCQEGKE YTDKAHFSSK CRRCRLCDEG HGLEVEINCT 120
121 RTQNTKCRCK PNFFCNSTVC EHCDPCTKCE HGIIKECTLT SNTKCKEEGS RSNLGWLCLL 180
181 LLPIPLIVWV KRKEVQKTCR KHRKENQGSH ESPTLNPETV AINLSDVDLS KYITTIAGVM 240
241 TLSQVKGFVR KNGVNEAKID EIKNDNVQDT AEQKVQLLRN WHQLHGKKEA YDTLIKDLKK 300
301 ANLCTLAEKI QTIILKDITS DSENSNFRNE IQSLV 335
```

MONOCLONAL ANTIBODIES TO THE APO-1 ANTIGEN

This application is a continuation of application Ser. No. 08/260,644 filed Jun. 16, 1994, which is a continuation-in-part of U.S. Ser. No. 07/691.106. filed Jun. 17, 1991, now abandoned, which is a continuation-in-part of International Application Number PCT/EP90/00111 filed Jan. 19, 1990 published as WO91/10448, Jul. 25, 1991.

BACKGROUND

Cell surface molecules play crucial roles in lymphocyte growth control. Such molecules may function as receptors for growth-stimulating cytokines or be associated with receptors and transmit signals essential for growth regulation. Receptor blockade or removal of the stimulating cytokines can lead to decreased lymphocyte growth. For example, withdrawal of interleukins slows human lymphocyte growth and finally leads to a characteristic form of cell death called "programmed cell death" or apoptosis. E. Duvall and H. H. Wyllie, *Immunol. Today* 7,115 (1986). Apoptosis is the most common form of eukaryotic cell death and occurs in embryogenesis, metamorphosis, tissue atrophy, and tumor regression. A. H. Wyllie, J. F. R. Kerr, A. R. Currie, *Int. Rev. Cytol.* 68:251 (1980). It is also induced by cytotoxic T lymphocytes and natural killer and killer cells; by cytokines such as tumor necrosis factor (TNF) and lymphotoxin (LT); and by glucocorticoids. The characteristic signs of apoptosis are segmentation of the nucleus, condensation of the cytoplasm, membrane blebbing (zeiosis), and DNA fragmentation into multimers of about 180 base pairs (called a "DNA ladder").

Recently, it has been shown that anti-CD3 induces apoptosis of immature thymocytes in vitro. C. A. Smith et al., *Nature*, 337:181 (1989). It has been suggested that CD3-triggered apoptosis might be responsible for negative selection of T cells in the thymus.

The selective induction of apoptosis in cells, such as diseased cells, could prove a useful therapeutic tool.

SUMMARY OF THE INVENTION

This invention pertains to a cellular surface antigen, designated APO-1, and to DNA encoding the antigen. The APO-1 antigen is associated with inhibition of cellular growth and induction of cellular apoptosis. The invention also pertains to binding agents, such as antibodies, fragments or analogues thereof, which specifically bind to APO-1 and induce inhibition of cell growth or cellular apoptosis. APO-1 has a relative molecular mass of about 50 kDa and is expressed by activated and some malignant lymphoid cells, and other normal and malignant cells. The binding of antibody to APO-1 induces apoptosis and thus, antibody or analogous binding agents can be used to induce growth inhibition or apoptosis in cells, such as lymphoid tumor cells, which carry the APO-1 antigen.

BRIEF DESCRIPTION OF THE FIGURE

The FIGURE shows the APO-1 amino acid sequence.

DETAILED DESCRIPTION OF THE INVENTION

The antigen APO-1 is a cellular membrane antigen having a relative molecular mass of approximately 50 kDa as determined by SDS-polyacrylamide gel electrophoresis. APO-1 is expressed by activated normal human lymphoid cells and lymphoid tumor cells, including B cell, T cell and HTLV-1-associated malignant cells such as adult T cell leukemic cells and other tumor and normal cells. The binding of anti-APO-1 antibody to cells expressing APO-1 results in growth inhibition and/or apoptosis. This effect is complement independent, mediated by antibody alone.

APO-1 can be isolated from the cellular membrane of cells (such as lymphoid cells) which express the antigen. Further, the cDNA encoding APO-1 can be cloned and expressed to provide the isolated antigen or portions of it. Isolated APO-1 can be used as an immunogen to raise anti-APO-1 antibody (polyclonal or monoclonal) or to screen for production of anti-APO-1 antibody by hybridomas, of chimeric anti-APO-1 antibody by transfected myelomas or of single chain anti-APO-1 antibody by transformed bacterial cells.

Antibodies which bind to APO-1 are useful for inducing inhibition of cell growth or apoptosis in cells that express APO-1 and are sensitive to induction of apoptosis. For this purpose, monoclonal anti-APO-1 antibodies are preferred. More specifically preferred are monoclonal antibodies of the IgG3 isotype. Monoclonal anti-APO-1 antibodies are produced by continuous (immortalized), stable, antibody-producing cell lines. The preferred antibody-producing cell lines are hybridoma cell lines. In principle, however, the cell lines can be derived from any cells which contain and are capable of expressing functionally rearranged genes which encode variable regions of the light and/or heavy chains of anti-APO-1 specificity. Preferably, the cell line should have the capability to assemble the chain (in the case of a single chain antibody) or chains into functional antibodies or antibody fragments. Intact, bifunctional antibodies are preferred for biological activity. Thus, lymphoid cells which naturally produce immunoglobulin are preferred.

Hybridoma cells which produce monoclonal anti-APO-1 antibodies can be made by the standard somatic cell hybridization procedure of Kohler and Milstein, *Nature*, 256:495 (1975). Briefly, a procedure is as follows: the monoclonal anti-APO-1 antibodies are produced by immunizing an animal with whole cells bearing APO-1 or membranes of these cells. Alternatively, the animals can be immunized with purified or partially purified natural or recombinant APO-1 or peptidic segments carrying one or more immunogenic epitopes of APO-1. Such peptides can be synthesized and conjugated to a carrier protein, such as keyhole limpet hemocyanin, to be used as an immunogen.

The preferred animal for immunization is the mouse. Various immunization protocols can be used. For example, mice can be given about $10^7$ APO-1-bearing cells once per week over a four-week period by intraperitoneal injection.

Antibody-producing lymphoid cells (e.g. splenic lymphocytes) are then obtained from the immunized animal and fused with immortalizing cells (preferably a myeloma or heteromyeloma). Many suitable myeloma cell lines are known in the art. For production of murine hybridomas, an example is the myeloma P3. X63. Ag8.653. See Kohler and Milstein, supra. Fusion of the spleen cells and fusion partner can be carried out in the presence of polyethylene glycol according to established methods. Techniques of electrofusion may also be used.

The resulting hybrid cells are clonally cultured and then screened for production of anti-APO-1 antibody. Hybridomas can be screened for secretion of antibodies which induce apoptosis against a cell line which expresses the APO-1 antigen and is sensitive to induction of apoptosis. An example of such a cell line is the malignant human B cell line SKW6.4. Additional such cell lines are set forth in Table 1 below. Purified or partially purified APO-1 can be used to screen for hybridomas that secrete antibodies of APO-1 specificity by standard immunoadsorbant assays. While anti-APO-1 antibodies of the IgG3 isotype are preferred for biological activity, believed to be due to their tendency to show self aggregation via the Fc portion of the antibody, screening for anti-APO-1 antibodies of other isotypes may be carried out in the presence of antibody crosslinkers such as protein A.

Although animal antibodies can be useful for human therapy, it may be preferable to convert animal antibodies to a form which may be better tolerated by a human. Monoclonal antibodies produced in murine or other animal systems can be converted to chimeric animal/human antibodies or to "near human" antibodies by standard techniques. Chimeric monoclonal antibodies of the IgG3 isotype are preferred for biological activity.

APO-1-binding fragments or analogues of anti-APO-1 antibodies can also be produced. For example, antibody fragments such as $F(ab')_2$, Fab and $F_v$ can be produced by enzyme digestion. In addition, synthetic oligopeptides representing Fab and $F_v$ analogues (single chain antibodies) can be produced in bacterial cells by genetic engineering techniques. For biological activity, intact bifunctional antibodies are preferred.

The antibodies can be used to induce growth inhibition or apoptosis in lymphoid cells (normal or malignant) or other cells bearing APO-1. For example, anti-APO-1 antibody can be used to treat tumors bearing the APO-1 antigen. As mentioned above, growth inhibition and/or apoptosis can be induced by antibody in various types of lymphoid cell malignancies which express APO-1. These lymphoid cell malignancies include malignancies of B or T cell lymphocytes. In particular, adult T cell leukemia, an HTLV-1 associated tumor, can be treated with anti-APO-1 antibody. In addition nonlymphoid tumors which bear APO-1 are candidates for the antibody therapy, e.g., some mammary carcinomas, sarcomas, colon carcinomas. Because anti-APO-1 antibodies of the invention kill activated T and B cells, they may be useful in treating autoimmune disease.

APO-1 may also be useful in treating AIDS. T-helper cells may be depleted by apoptosis. Auto-antibodies against APO-1 have been detected in AIDS serum. HIV genes may increase the susceptibility of T cells to apoptosis, either by direct infection or by HIV gene product taken up by infected or noninfected cells. Thus, a therapeutically effective amount of the APO-1 antigen can be administered as a competitive inhibitor. The antigen in this context acts as a decoy molecule thereby inhibiting the binding of the apoptosis inducing antibodies to cells bearing the antigen.

The anti-APO-1 antibodies are administered to a patient afflicted with the tumor in an amount that induces growth inhibition or apoptosis of APO-1 bearing cells. Effective anti-tumor dosages and dosage regimens can be determined for the various types of tumors.

The antibody will ordinarily be administered as a pharmaceutical composition consisting essentially of a therapeutically effective apoptosis-inducing amount and a pharmaceutically acceptable carrier.

Monoclonal antibodies or APO-1 antigen may be administered by any means that enables the active agent to reach the agent's site of action in the body of a mammal. In the case of the antibodies of this invention, the primary focus is the ability to reach and bind with the desired APO-1 bearing cells. Because proteins are subject to being digested when administered orally, parenteral administration, e.g., intravenous, subcutaneous, or intra-muscular, would ordinarily be used to optimize absorption.

Monoclonal antibodies may be administered either as individual therapeutic agents or in combination with other therapeutic agents. They can be administered alone, but are generally administered with a pharmaceutical carrier selected on the basis of the chosen route of administration and standard pharmaceutical practice.

For parenteral administration, the antibody or antigen can be formulated as a solution, suspension, emulsion or lyophilized powder in association with a pharmaceutically acceptable parenteral vehicle. Examples of such vehicles are water, saline, Ringer's solution, dextrose solution, and 5% human serum albumin. Liposomes and nonaqueous vehicles such as fixed oils may also be used. The vehicle or lyophilized powder may contain additives that maintain isotonicity (e.g., sodium chloride, mannitol) and chemical stability (e.g., buffers and preservatives). The formulation is sterilized by commonly used techniques.

Suitable pharmaceutical carriers are described in *Remington's Pharmaceutical Sciences*, A. Osol, a standard reference text in this field. Useful pharmaceutical dosage forms for administration of the compounds of this invention by injection can be prepared, for example, by dissolving 1.5% by weight of active ingredient in 0.9% sodium chloride solution.

Lymphoid tumors which express APO-1 can also be treated extracorporeally. Blood cells or blood leukocytes are removed from the patient and contacted with anti-APO-1 antibodies in amounts sufficient to reduce or eliminate tumor cells. After treatment, the blood cells or leukocytes are returned to the patient.

The antibodies can also be used diagnostically to determine APO-1 expression by cells. For example, the anti-APO-1 antibodies can be used to define subsets of normal and malignant lymphocytes based upon the expression of APO-1. For this purpose, conventional assays for determination of cellular surface antigens can be used. For example, a sample of cells to be tested is incubated with an anti-APO-1 antibody under conditions which allow the antibody to bind APO-1 on the cell surface. A second antibody directed against the anti-APO-1 antibody is used to detect binding (e.g. if the anti-APO-1 antibody is a mouse antibody, the second antibody can be a goat anti-mouse antibody). The second antibody is labeled, preferably with an enzyme or a fluorescent molecule. After incubation of the cells with the labeled antibody, the label associated with the cell is detected as indication of the APO-1 expression by the cell.

cDNA encoding the APO-1 antigen has been isolated as described in Example 3. The deduced amino acid sequence of the APO-1 antigen is shown in the FIGURE. The isolated cDNA can be used, for example to produce the APO-1 antigen by conventional recombinant techniques.

The invention is illustrated further by the following examples.

EXAMPLES

Example 1

Methods

Production of Anti-APO-1 Antibodies

BALB/c mice were immunized once per week over a 4-week period by intraperitoneal injection of $1 \times 10^7$ SKW6.4 cells. Any cell line expressing the APO-1 antigen (see Table 1) may be used. Four days after the last injection, spleen cells from immunized animals were fused with the P3. X63. Ag8.653 myeloma cells (G. Kohler and C. Milstein, *Nature*, 256:495 (1975)). Twelve days after fusion culture supernatants from wells positive for growth of hybridoma cells were tested for their ability to inhibit growth of SKW6.4 cells. Hybridomas that produced blocking monoclonal antibodies (MAbs) were cloned three times by limiting dilution at a concentration of 0.5 cells per well. MAbs were purified from serum-free culture supernatant by means of a protein A-Diasorb affinity adsorption column (Diagen, Dusseldorf, FRG). Bound MAbs were eluted with 0.1M NaCl and 0.1M glycine, pH 2.8, dialyzed against phosphate-buffered saline and sterilized. The isotype of the MAbs was determined by enzyme-linked immunosorbent assay (S. Kiesel, et al., *Leuk. Res.*, 11:1119 (1987)) with isotype-specific goat anti-mouse Ig that had been conjugated with horse-radish peroxidase (Dunn, Asbach, FRG).

Determination of binding affinity and number of binding sites

Affinity and number of anti-APO-1 binding sites per cell were determined by Scatchard analysis as described (I. von Hoegen et al., *Eur. J. Immunol.*, 19:239 (1989)). Briefly, MAbs were iodinated by the IODO-Gen method (P. J. Fraken and J. C. Speck, *Biochem. Biophys. Res. Commun.*, 80:849 (1980)). Aliquots of $5\times10^5$ cells were resuspended in 200 µl of culture medium containing 0.1% $NaN_3$, and different concentrations of $^{125}I$-labeled MAbs. After incubation at 4° C. for 4 hours, two 95 µl portions were removed and centrifuged as described above by von Hoegen et al.

SDS polyacrylamide gel electrophoresis (SDS-PAGE) for molecular mass determination Cells ($3\times10^6$) were labeled with 60 µCi of $^{75}Se$-labeled methionine (Amersham, Braunschweig, FRG) in 6 ml of methionine-free culture medium (Biochrom, Berlin) for 48 hours. After washing, the cells were incubated in either control MAb or anti-APO-1 (1 µg/ml) at 4° C. for 45 minutes. The cells were washed and resuspended in lysis buffer (tris-buffered saline, pH 7.3, 1% Nonidet P-40, 1 mM phenylmethylsulfonyl fluoride, 0.1% aprotinin) at room temperature for 30 minutes. The lysates were centrifuged and supernatants were incubated with protein A-Sepharose beads (Pharmacia, Uppsala, Sweden) at 4° C. for 1 hour. The immune complexes were washed four times with buffer (tris-buffered saline, pH 7.3, 0.25% Nonidet P-40) and resuspended in SDS-PAGE sample buffer containing 5% SDS and 5% 2-mercaptoethanol. The samples were heated to 95° C., centrifuged, and counts per minute of the supernatants were determined in a γ-counter. A total of 15,000 cpm were loaded in each lane and analyzed by a 10% SDS-PAGE (V. K. Laemmli, *Nature*, 277:680 (1970)). The gel was dried and subjected to autoradiography.

Induction of growth inhibition and apoptosis by anti-APO-1

The T cell line CCRF-CEM (ATCC #CLR8436) was cultured in the presence of purified MAb (1 µg/ml) in a microtiter plate for 2 hours before photography. The CCRF-CEM.S2 subclone was obtained by cloning cells under limiting dilution conditions from the CCRF-CEM T cell line at one cell per well in 96-well microtiter plates. CCRF-CEM.S2 was selected because of its high sensitivity to programmed cell death induced by anti-APO-1 antibody (500 ng/ml) as measured by microscopic inspection in a 0.5-hour (30 minute) culture.

CCRF-CEM.S2 cells ($10^6$ per milliliter) were incubated with MAb (1 µg/ml) in culture medium at 37° C. At various times, aliquots of $10^6$ cells were removed and DNA was prepared.

SKW6.4 cells were either incubated with the isotype-matched control MAb FII20, FII23 (nonbinding MAb), or anti-APO-1 in microcultures for 24 hours before labeling with [$^3H$]-thymidine for a further 4 hours. The data represent the mean of duplicate cultures with a variation of less than 5%. The cells were cultured in RPMI 1640 medium (Gibco, Grand Island, N.Y.), supplemented with 2 mM L-glutamine, streptomycin (100 µg/ml), penicillin (100 U/ml), 20 mM Hepes buffer pH 7.3, and 10% heat-inactivated fetal bovine serum (Conco Lab-Division, Wiesbaden, FRG). For microcultures $1\times10^4$ cells per well were cultured in duplicates in flat bottom 96-well microtiter plates (Tecnomara, Fernwald, FRG) (200 µl final volume per well). After 24 hours, the cells were labeled with 0.5 µCi of [$^3H$]-thymidine (Amersham, Braunschweig, FRG)) for 4 hours. Before harvesting, the microcultures were examined by microscopic inspection. For DNA fragmentation $1\times10^6$ cells were washed with cold phosphate-buffered saline and disrupted with NTE buffer, pH 8 (100 mM NaCl, 10 mM Tris-HCl, 1 mM EDTA) containing 1% SDS and proteinase K (0.2 mg/ml). After incubation for 24 hours at 37° C., samples were extracted twice with phenol plus chloroform (1:1, v/v) and precipitated by ethanol. The DNA was dissolved in 38 Al of NTE buffer and digested with ribonuclease (1 mg/ml) for 30 minutes at 37° C. To each sample 10 µl of loading buffer containing 15% Ficoll 400 (Pharmacia, Uppsala, Sweden), 0.5% SDS, 50 mM EDTA, 0.05% bromophenol blue, 0.05% xylene cyanol in TBE buffer (2 mM EDTA, 89 mM boric acid, 89 mM Tris, pH 8.4) were added. The mixture was loaded onto a 1% agarose gel and stained after electrophoresis with ethidium bromide (0.5 µg/ml).

Reactivity of anti-APO-1 with different cells

Aliquots of $10^6$ cells were incubated at 4° C. in 100 µl of medium with control MAb (FII23 or I3BI) or anti-APO-1 for 30 minutes. Then the cells were washed and stained with fluorescein isothiocyanate-coupled goat anti-mouse IgF(ab')$_2$ (70 µg/ml) and analyzed by a cytofluorograph (Ortho Diagnostic Systems, Westwood, Massachusetts).

For determination of the effect of anti-APO-1 on tritiated thymidine uptake, cells ($10^4$ per well) were cultured in the presence of MAb (500 ng/ml) for 24 hours and labeled with [$^3H$]-thymidine for 2 hours before harvest; the data in Table 1 represent the mean of duplicate cultures with a variation of less than 5%.

Leukemic cells from patients were obtained as follows. Bone marrow cells isolated from the patients were morphologically >95% blasts and showed the following phenotype: pre T-ALL, cytoplasmic $CD3^+$, $CD5^+$, $CD7^+$, $CD34^+$, $Tdt^+$, $CD2^-$, surface $CD3^-$, $CD4^-$, and $CD8^-$; T-ALL, $CD2^+$, cytoplasmic $CD3^+$, $CD5^+$, $CD7^+$ and $Tdt^+$, surface $CD3^-$, $CD4^-$, $CD8^-$ and $CD34^-$; common-ALL $CD10^+$, $CD19^+$, $CD22^+$, $CD24^+$, $CD20^-$. The effect of anti-APO-1 on these leukemic cells was not tested, because they died under normal culture conditions.

Normal human lymphocytes were obtained as follows. Peripheral blood mononuclear cells (PBMC) from healthy volunteers were isolated by Ficoll Paque (Pharmacia Inc., Uppsala, Sweden) density gradient centrifugation. Adherent cells were removed by adherence to plastic culture vessels overnight. T cells were isolated from PBMC by rosetting with 2 amino-ethylisothyouronium-bromide (AET)-treated sheep red blood cells as described by Madsen et al., (*J. Immunol. Methods*, 33:323 (1980)). Freshly prepared resting T cells ($2\times10^6$ per milliliter; 96% $OKT11^+$, 1% $Tac^+$) were activated with phytohemag-glutinin-M (50 µg/ml) and PMA (10 ng/ml) (Sigma Chemical Co., Munich, FRG). Two, 7, and 12 days later the T cells were fed with 20 to 30 U/ml of recombinant human interleukin-2 (20 to 30 U/ml). T cells (5×10⁵ per milliliter) activated for 12 days (90% OKT11⁺; 60% Tac⁺) were cultured in the presence of FII23 or anti-APO-1 (1 μg/ml) in triplicates for 24 hours and then labeled with [³H]-thymidine for a further 17 hours (see above).

Resting B cells (35.8% CD19⁺) were isolated by two rounds of resetting as above, followed by separation via a Sephadex G-10 column as described by Jerrells et al., *J. Immunol. Methods*, 32:11 (1980). For activated B cells, PBMC were adjusted to 2×10⁶ cells per milliliter and cultured in the presence of pokeweed mitogen at 10 μg/ml (Serva, Heidelberg, FRG) for 6 days. Dead cells and T cells were then eliminated by resetting with AET-treated sheep red blood cells and subsequent centrifugation over Ficoll Paque. The interphase cells were used as activated B cells (84% sIgM⁺).

Effect of anti-APO-1 on tumor growth in vivo

BJAB cells (4×10⁷) were injected subcutaneously into the left flank of nu/nu mice. After 5 weeks (day 0) the mice were injected with 500 μg of MAb into the tail vein. Fourteen days later the size of the tumors was measured at the base of the tumor.

Localization of anti-APO-1 in tumor xenografts

Localization of anti-APO-1 in xenografts of BJAB in nu/nu mice and induction of apoptosis of the tumor was determined. Anti-APO-1, labeled with ¹²⁵I, was injected in mice which had been previously injected with BJAB cells. Ten days after intravenous injection of 500 μg of MAb per mouse the remaining tumor tissue was removed and fixed with formalin. The tumors were excised and embedded in methylcellulose and 20-μm cryotome sections were prepared. Paraffin sections of the tumor were stained with haematoxylin/eosin. Lyophilized sections were placed on a Kodak X-omat AR film for autoradiography.

Results

A MAb (anti-APO-1) was identified that blocks growth and induces apoptosis of SKW6.4 cells. The anti-APO-1 (IgG3, κ, $K_D=1.9\times10^{-10}$) bound to approximately 1–4×10⁴ sites on the surface of SKW6.4 cells. The antibody specifically immunoprecipitated an endogenously synthesized protein antigen (APO-1) from SKW6.4 cells which, under reducing conditions, was observed on SDS-polyacrylamide gel electrophoresis (SDS-PAGE) as a main band of about 50 kDa. Apart from actin (43 kDa), which was nonspecifically precipitated with IgG3, anti-APO-1 also specifically immunoprecipitated a minor band of 25 kDa. This 25-kDa protein might either represent a degradation product or be noncovalently associated with the about 50-kDa protein.

There are two major modes of death in nucleated eukaryotic cells. Necrosis as a result, for example, of complement attack is characterized by swelling of the cells and rupture of the plasma membrane caused by an increase in permeability. Cells that undergo apoptosis, however, show a different biochemical and morphological pattern. This pattern corresponds to the one induced by anti-APO-1: condensation of the cytoplasm, membrane blebbing, and endonuclease-induced DNA fragmentation (A. H. Wyllie, *Nature*, 284:555 (1980)) into multimers of approximately 180 bp. Affinity-purified anti-APO-1 induced growth retardation and cell death, which was not observed with either an isotype-matched, control MAb (FII20) [anti-MHC(major histocompatibility complex) class I antigens] or the nonbinding MAb FII23. Abrogation of [³H]-thymidine incorporation along with increased trypan blue uptake into dead cells were observed, and growth of 10⁴ SKW6.4 cells in 200-μl cultures was blocked by more than 95% by an anti-APO-1 concentration of only 10 ng/ml. The specificity of cell death induced by anti-APO-1 becomes evident from the fact that the following additional control MAbs were inactive for induction of apoptosis: 18 nonbinding and 9 binding MAbs of the IgG3 isotype (tested by immunofluorescence on SKWG.4 cells) and a panel of MAbs directed against known antigens on the cell surface of SKW6.4 cells including CD19, CD20, CD22, MHC class II, IgM (immunoglobulin M), and the SKW6.4 idiotype.

Cell death induced by anti-APO-1 was complement-independent and occurred under serum-free culture conditions or in culture medium plus serum inactivated at 56° C. for 30 minutes. It differed from death mediated by complement-dependent lysis by: (i) morphology and formation of a DNA ladder, (ii) exogenous $Ca^{2+}$ independence and (iii) delayed ⁵¹Cr release from radiolabeled target cells. The kinetics of membrane blebbing induced by anti-APO-1 (within 30 minutes) was not influenced by the presence of 10 mM EDTA or EGTA. In addition, endonuclease-mediated DNA fragmentation induced by anti-APO-1 was not inhibited by the $Ca^{2+}$ channel blockers Furamicin (50 μM) or Nifedipin (50 μM). When ⁵¹Cr-labeled SKW6.4 cells were incubated with anti-APO-1 (1 μg/ml) for 2, 4, 8 and 24 hours, the specific ⁵¹Cr release ((R. C. Duke et al., *Proc. Natl. Acad. Sci. U.S.A.*, 80:6361 (1983)) was found to be 2.9%, 7.6%, 21.3% and 332.5%, respectively. Trypan blue uptake was measured at the same time points: 2.5%, 4.7%, 10.6% and 73.6%, respectively, of the cells were trypan blue positive. In contrast, 2 hours after the addition of MAbs plus complement the specific ⁵¹ Cr release was 108.7% and 92.7% of the cells stained with trypan blue. These experiments indicate that cell death induced by anti-APO-1 is fundamentally different from antibody- and complement-dependent cell lysis.

To assess the specificity of anti-APO-1, a restricted panel of tumor cell lines was screened for expression of APO-1 and susceptibility to growth inhibition and apoptosis. APO-1 was expressed on various human lymphoid B and T cell lines and was not found on a gibbon or mouse T cell line or a human monocytic cell line (Table 1). Anti-APO-1 blocked proliferation of the APO-1-positive cell lines listed in Table 1 via induction of apoptosis, and formation of a DNA ladder was observed in each case. Two hours after addition of the MAbs (1 μg/ml) the genomic DNA of each tumor line was isolated and analyzed on agarose gels as described above. Inhibition of [³H]-thymidine uptake by anti-APO-1 was paralleled by fragmentation of the genomic DNA. This was not observed after treatment with control MAb (I3BI).

Expression of APO-1 was not restricted to cell lines in vitro but could be found on leukemic cells freshly isolated from patients (Table 1). Since APO-1 was not found on all leukemic cells, anti-APO-1 may define a subpopulation of leukemias.

We also screened human B and T cells for expression of APO-1. We did not detect APO-1 on resting B cells. However, APO-1 was expressed on activated B cells (Table 1) and IgM secretion was reduced approximately fourfold by 3 days of treatment with anti-APO-1. Activated B cells (10⁶ per milliliter) were incubated in the presence of MAb FII23 or anti-APO-1 at 1 μg/ml. After 3 days the culture supernatants were collected and the IgM concentration measured with a human IgM-specific ELISA containing HRPO-conjugated goat anti-human IgM (Medac, Hamburg, FRG). IgM secretion after treatment with FII23 or anti-APO-1 was 2100 and 550 ng/ml, respectively).

TABLE 1

Reactivity of anti-APO-1 with different cells

| Type | Designation | Cells positive for APO-1 (%) | Relative fluorescence intensity (anti-APO-1/ control) | Effects of MAbs on cells* [$^3$H] thymidine uptake ($10^3$ cpm) Control | Anti-APO-1 |
|---|---|---|---|---|---|
| Malignant cell lines | | | | | |
| Hu B cells | SKW6.4 | 98 | 11.1 | 30.0 | 0.02 |
| | CESS | 95 | 12.0 | 23.0 | 0.1 |
| | BJAB | 80 | 2.1 | 70.0 | 7.0 |
| | OCI.LY1 | 0 | 1 | 14.5 | 15.8 |
| Hu T cells | Jurkat | 83 | 2.3 | 20.3 | 8.1 |
| | Molt | 91 | 2.4 | 35.7 | 0.6 |
| | CCRF-CEM | 64 | 1.9 | 16.2 | 0.5 |
| Hu myeloid cells | U937 | 5 | 0.97% | 62.2 | 60.5 |
| Gibbon T cells | MLA 144 | 0 | 0.96 | 34.3 | 35.0 |
| Mouse T cells | EL4 | 0 | 1 | 44.8 | 45.3 |
| Leukemic cells from patients | | | | | |
| Pre T-ALL | B.M. | 54 | 4.4 | | |
| T-ALL | D.A. | 53 | 3.2 | | |
| Common ALL | W.N. | 72 | 5.0 | | |
| Normal human lymphocytes | | | | | |
| T cells | Resting | 3 | 1.36 | | |
| | Activated | 89 | 7.4 | 22.4 | 0.23 |
| B cells | Resting | 0 | 0.9 | | |
| | Activated | 91 | 1.1 | | |

Peripheral resting T cells did not express APO-1. Activated T cells, however, expressed APO-1 and anti-APO-1 induced apoptosis and growth inhibition of these cells (Table 1). Thus, our data suggest that APO-1 is a species-specific antigen expressed on activated or malignant lymphocytes.

The striking effect of anti-APO-1 in vitro prompted us to test its effect on tumor growth in vivo. Although the Epstein-Barr virus (EBV)-negative, Burkitt-like lymphoma BJAB was the least sensitive to anti-APO-1 of the B cell panel in Table 1 and expressed only approximately $1.5 \times 10^4$ APO-1 epitopes per cell, BJAB was selected for in vivo experiments. The reason for this choice was that only BJAB grew to large tumor masses in unirradiated nu/nu mice. Five weeks after injection of BJAB cells the nu/nu mice carried tumors with a diameter of approximately 1.0 to 2.5 cm. These mice were injected intravenously with purified anti-APO-1 (500 μg per mouse) or the same quantities of various isotype-matched control antibodies (FII20, anti-MHC class I antigens, recognizing $5.8 \times 10^5$ sites per cell; or one of the two nonbinding MAbs FII23 and I3BI). As a control anti-APO-1 (500 μg per mouse) was also injected into three nu/nu mice carrying the APO-1-negative B cell tumor OCL.LY1 with tumor diameters of 1.5, 1.8, and 3.4 cm, respectively (OCI-LYI was obtained from H. Messner, Ontario Cancer Institute, Toronto, Canada) (see also Table 1). Two days after anti-APO-1 injection, a whitish discoloration of the BJAB tumors was observed that was followed by rapid tumor regression. Macroscopic tumor regression was seen in 10 of 11 treated mice within less than 14 days. The control antibodies had no effect. In addition, no tumor regression was observed in the mice carrying OCI.LYI, as expected.

To demonstrate proper localization and enrichment of the injected antibodies, labeled MAbs were visualized by autoradiography of sections of the BJAB tumor tissue. These autoradiographs showed a pronounced binding of anti-APO-1 in the periphery but only sparse accumulation in the center of the tumor. The binding control Mab FII20 showed a qualitatively similar binding pattern. There was no localization of the nonbinding control MAb FII23 above background. Furthermore, paired label experiments (D. Pressman et al., Cancer Res., 17:845 (1957)) with labeled anti-APO-1 and FII23 revealed that the specific enrichment of anti-APO-1 over FII23 in the tumor was four- and sixfold after 48 and 96 hours, respectively.

The main purpose of our experiments was to assess whether anti-APO-1 can also act in vivo. Therefore, the tumor-bearing mice only received one intravenous injection of anti-APO-1 at a dose in the range used in MAb therapies. In other therapy schedules, however, MAbs are injected repeatedly (see e.g., S. L. Brown et al., Blood, 73:651 (1989)). In our experiments regrowth of the BJAB tumor was observed in three of the ten mice in which tumor regression had been observed. Regrowth was observed at the margin of the original tumor approximately 3 months after the initial macroscopic tumor regression. One of these tumors was removed and found to express APO-1 by immunofluorescence and to be sensitive to anti-APO-1 in vitro at a MAb concentration similar to the original in vitro BJAB tumor cell line (Table 1).

To determine the histology of the regressing BJAB tumors we prepared thin sections of tumors from MAb-treated nu/nu mice. Ten days after intravenous injection of FII20, BJAB appeared as a solid tumor composed of densely packed large blasts with numerous mitoses, some tumor giant cells, and rare apoptotic figures. The tumor was penetrated by host vessels. In contrast, almost all remaining BJAB cells of mice treated with anti-APO-1 showed severe cytopathic changes including nuclear pycnosis and cellular edema most pronounced in perivascular microareas. These morphological changes are characteristic of apoptosis.

Taken together, these data strongly suggest that apoptosis is induced by anti-APO-1 antibody and is the mechanism of death and regression of BJAB tumor cells in vivo. The fact that FII20, which strongly binds to the cell surface of BJAB tumor cells, did not cause regression of BJAB also precludes the possibility that killer cells or complement that might have bound to anti-APO-1 may have been involved in the growth inhibition and tumor regression.

Example 2

Materials and Methods

Cell culture medium and reagents:

All cells were cultured in RPMI 1640 supplemented with L-glutamine (2 mM final concentration), streptomycin (100 μg/ml), penicillin (100 U/ml), HEPES (25 mM final concentration) and 10% fetal calf serum (FCS, Advanced Biotechnologies Inc., Silver Spring, Md.). Recombinant IL2 (final concentration 20 U/ml) and recombinant IL-4 (final concentration of 5 ng/ml) were purchased from Boeringer Mannheim, FRG. The cultures were kept at 37° C. in 95% air, 5% $CO_2$ at 90% relative humidity.

Cell lines and leukemic cells from ATL patients:

Various HTLV-1 transformed T cell lines were investigated. C91/P1 is a cord blood T cell line transformed by HTLV-I and continuously kept in culture in the presence of IL-2. All other T cell lines used were originally derived from patients with ATL. JGCL and DCL are IL-2 dependent cell lines. MJCL and MT1 are IL-2 independent cell lines which still respond to IL-2 with enhanced proliferation. CRII2 and HUT102 are the prototype HTLV-I positive leukemic cell lines in which HTLV-I was originally described. Growth of these cell lines does not depend on IL-2 in the culture medium.

As a prototype APO-1 positive and anti-APO-1 sensitive cell line, B cell line SKW6.4 was included as a control in all experiments. Trauth et al., Science, 245:301–305 (1989).

Thawed leukemic cells from five patients with ATL were used for the experiments. The cells from patients with a high leukemic cell count were frozen and stored in liquid nitrogen in medium containing 20% FCS and 10% DMSO. After careful thawing, there was a considerable loss of cells which appears to be characteristic for ATL cells. Viable cells were isolated after thawing by density gradient centrifugation (LSM, Organon Technika Corp., Durham, N.C.) and cultured in vitro for further experiments.

Immunofluorescence analysis

Immunofluorescence staining was determined by flow cytometry with the following antibodies: anti-Tac-antibody was used at 1 $\mu$g/$10^6$ cells. Anti-APO-1 (IgG3, κ) and an isotype matched control non-binding antibody were used as a 10% dilution of the original hybridoma supernatant. Antibodies against CD3, CD4, CD8 were purchased from Becton Dickinson (Mountain View, Calif.) and used according to the manufacturer's instructions. For cell surface staining 1×$10^6$ cells in 100 $\mu$l medium were incubated with the appropriate dilutions of the antibodies in phosphate buffered saline (PBS) containing 1% FCS and 0.3% Na-azide. Prior to the addition of antibodies human IgG was added to a final concentration of 100 $\mu$g/ml. After incubation for 30 minutes, cells were washed and incubated with a second FITC labeled goat-anti-mouse Ig antibody (TAGO, Burlingame, Calif.).

cell proliferation

Cell proliferation at the cell concentrations indicated was determined in 96 well flat bottom plates Costar, Cambridge, Mass.). After the time indicated 0.1 $\mu$Ci of [$^3$H]-thymidine ($^3$H-TdR, DuPont NEN, Boston, Mass.) was added to each culture well. Proliferation was assessed by harvesting the plates and $^3$H-TdR uptake was determined in a liquid scintillation counter.

cell death

After incubation of cells with the anti-APO-1 antibody viability and cell death were determined by the trypan blue dye exclusion method.

Results

PO-1 expression on HTLV-I Positive T cell lines

We first investigated the expression of the APO-1 antigen on various T cell lines originally established from patients with ATL. By immunofluorescence staining all cell lines used displayed a characteristic mature T cell phenotype (CD4$^+$, CD8$^-$, Tac$^+$). Only the JGCL cell line was CD4$^-$, CD8$^+$, Tac$^+$. Strong expression of the APO-1 antigen was found on all cell lines. The intensity of APO-1 expression was comparable to the expression found on activated normal T cells or on APO-1 positive B and T cell lines.

Inhibition of proliferation and anti APO-1 induced apoptosis of HTLV-I positive T cell lines To assess growth inhibition and apoptosis of HTLV-I positive T cell lines by anti-APO-1 the cell lines were cultured in vitro for two days in the presence of various concentrations of anti-APO-1. As a control parallel cultures were incubated with 10 $\mu$g/ml of an isotype-matched non-binding control antibody. The proliferation of all T cell lines tested was inhibited by anti-APO-1 antibody. As a positive control, SKW6.4, the highly anti-PO-1 sensitive cell line, a B lymphoblastoid line against which anti-APO-1 was originally raised (See example 1) was included in each experiment. Growth inhibition of various cell lines, e.g. JGCL and MJCL, was quantitatively comparable to growth inhibition of the SKW6.4 cell line.

All highly sensitive cell lines showed the characteristic morphological features of apoptosis (membrane blebbing, condensation of nucleus and cytoplasm) after incubation with anti-APO-1. After two days of incubation with anti-APO-1 50–98% of the cells were found to be dead by the trypan blue dye exclusion method.

Expression of APO-1 on cultured ATL cells

Following observation of APO-1 expression and induction of apoptosis by anti-APO-1 on the HTLV-1 positive T cell lines, an experiment was designated to test whether APO-1 is also expressed on the leukemic cells from patients with ATL. Thawed cells from frozen peripheral blood cells (more than 50% malignant T cells) were investigated. The recovery of ATL cells after thawing is usually low. After thawing, recovery ranged from 2–35%. These cells showed low Tac and variable APO-1 expression (3–15% and 1–53% positive cells, respectively). For further studies, the cells were cultured in medium supplemented with IL-2 for 5 days. Under these conditions ATL cells increased APO-1 and Tac expression. Again the intensity of APO-1 expression was comparable to the one on HTLV-I transformed T cell lines and on other sensitive cells such as activated T cells or malignant T or B cell lines.

Effect of anti-APO-1 on proliferation of ATL cells in vitro

Since APO-1 was expressed on cultured ATL cells an experiment was designed to determine whether anti-APO-1 inhibited proliferation of these cells in vitro. ATL cells were cultured either in medium alone or in medium plus IL-2 and IL-4. The reason for culturing the cells in IL-2 or IL-4 was that in some cases ATL cells showed a proliferative response to IL-2 of IL-4 without prior activation.

After thawing 2×$10^5$ cells/well were cultured in a 96 well flat bottom plate. Where indicated IL-2 (20 U/ml) or IL-4 (5 ng/ml) were added. The cells were cultured for 3 days in the presence of medium alone or with 1 $\mu$g/ml anti-APO-1 or 1 $\mu$g/ml isotype-matched control antibody. 0.5 $\mu$Ci of $^3$H-TdR were added for the last 8 hours of culture. Proliferation was measured by determining $^3$H-TdR uptake. Data are given as the absolute cpm (mean) for culture in medium alone (cpm control) and the percentage of inhibition of $^3$H-TdR uptake by anti-APO-1. The standard deviation for triplicate cultures was less than 10%. Incubation with the isotype-matched control antibody had no effect compared to culture in medium alone. Table 2 shows that ATL cells from patients 1 and 4 already exhibited a high spontaneous proliferation. In cells from patients 3, 4 and 5 proliferation was augmented by addition of IL-2 or IL-4. Addition of anti-APO-1 to the cultures greatly inhibited the proliferation of the malignant cells. Incubation with a control antibody did not have any effect.

TABLE 2

Effect of anti-APO-1 on proliferation of ATL cells in vitro

| Cells from Patient No. | Incubation with | Proliferation of cells in medium (cpm) | Growth inhibition by anti-APO-1 (%) |
|---|---|---|---|
| 1 | medium | 24682 | 82 |
|   | IL-2 | 18872 | 73 |
|   | IL-4 | 49343 | 61 |
| 2 | medium | n.d. | — |
|   | IL-2 | 110167 | 99 |
|   | IL-4 | 43674 | 99 |
| 3 | medium | 420 | 18 |
|   | IL-2 | 3700 | 89 |
|   | IL-4 | 5253 | 97 |
| 4 | medium | 36672 | 48 |
|   | IL-2 | 46716 | 52 |
|   | IL-4 | 61503 | 60 |

TABLE 2-continued

Effect of anti-APO-1 on proliferation of ATL cells in vitro

| Cells from Patient No. | Incubation with | Proliferation of cells in medium (cpm) | Growth inhibition by anti-APO-1 (%) |
|---|---|---|---|
| 5 | medium | 629 | 10 |
|   | IL-2 | 1724 | 71 |
|   | IL-4 | 2110 | 81 |

Induction of apoptosis of cultured ATL cells by anti-APO-1 treatment in vitro

To investigate the induction of apoptosis of ATL cells by anti-APO-1, thawed ATL cells were first cultured for five days in the presence of IL-2 (20 U/ml). During this time no net gain in cell numbers during culture was observed. The cultured cells were then incubated for 48 hours with 1 μg/ml anti-APO-1 or control antibody, respectively. Under these conditions 75–100% of ATL cells were dead after anti-APO-1 treatment.

Example 3
Purification and cloning of cDNA encoding the APO-1 Antigen

To characterize the APO-1 cell surface molecule and to better understand its role in induction of apoptosis, the APO-1 protein was purified to homogeneity from membranes of SKW6.4 lymphoblastoid cells. Endoproteinase cleaved peptides of the APO-1 protein were subjected to amino acid sequencing and oligonucleotides were designed on the basis of the peptide sequences and used to identify a full length APO-1 cDNA clone from an SKW6.4 cDNA library by hybridization techniques.

The APO-1 antigen was purified from membranes of SKW6.4 cells by solubilization with sodium deoxycholate and a combination of affinity chromatography and reversed phase HPLC. Membranes from $5 \times 10^{10}$ SKW6.4 cells prepared by a Tween-40 method (J. Arvieux and A. F. Williams, in *Practical ADproach Series: Antibodies*, D. Catty, Ed. (IRL Press Ltd, Oxford, England, 1988), pp. 113–136) were solubilized with 2% sodium deoxycholate, 0.01M Tris-HCl, 0.1% $NaN_3$, 1 mM PMSF (pH 8.1) incubated for 1 hour at 4° C. and centrifuged at 100,000 g for 1 hour. The supernatant was then applied to a mouse FII23 IgG3-Sepharose 4B column (3 mg MAb:4 ml beads) (to remove aggregates and minimize non-specific binding) which was connected to an IgG3 anti-APO-1 column (9 mg MAb:12 ml beads). The anti-APO-1 affinity column was washed first with 0.1% sodium deoxycholate, 0.01M Tris-HCl, 0.1% $Nan_3$, 1 mM PMSF, pH 8.1 (buffer), second with 0.15M NaCl in the above buffer and finally with buffer 1 again. Bound material was eluted with 0.05M diethylamine/HCl, 0.1% sodium deoxycholate, 0.1% $Nan_3$, 0.1% PMSF, pH 11.5, and neutralized. Fractions with high APO-1 antigenic activity were pooled, brought to 10% acetonitrile and chromatographed at 1 ml $min^{-1}$ on two subsequent reversed phase HPLC columns (PLRP-S column, 300 A, 8 μm, 250×4.6 mm, Polymer Laboratories, Shropshire, UK) using a linear gradient from 0–100% B (70% acetonitrile, 0.1% trifluoroacetic acid in $H_2O$) in 30 minutes.

For detection and quantification of APO-1, the purification was followed by a rapid ELISA method. Briefly, APO-1 containing extracts were coated onto immunoassay plates and APO-1 was detected with IgG2b anti-APO-1 and goat-anti-mouse IgG2b/HRPO-conjugated.

The purified APO-1 antigen was analyzed by SDS-PAGE. A single band of apparent molecular mass of about 48,000 Da was revealed. The western blot was only developed under non-reducing conditions. Therefore, the epitope recognized by anti-APO-1 was dependent on intramolecular disulfide bonds. Further biochemical analysis showed that APO-1 is a single chain glycoprotein with a p.I. of 5.4 to 5.7 which is predominantly glycosylated by N-glycosidic polysaccharides. The purified APO-1 protein was able to inhibit anti-APO-1 induced growth inhibition and apoptosis of SKW6.4 cells. This was demonstrated by incubating $2 \times 10^4$ SKW6.4 cells for 24 hours with various amounts of purified APO-1 antigen in the presence of either 20 ng/ml isotype-matched non-binding control MAb FII23 or 20 ng/ml anti-APO-1. Inhibition of cell death (%) was measured by $^3$H-TdR incorporation after pulsing cells with 0.5 μCi $^3$H-TdR for the last 6 hours of the culture according to the quotient ($^{cpm}$APO-1-anti-APO-1/$^{cpm\ APO-}$1-coMAb)× 100.

10 μg (210 pmol) purified APO-1 were digested with Asp-N endoproteinase (Boehringer Mannheim, FRG) according to the manufacturer's instructions to generate peptides that were separated by C8 reversed phase using a 2.1×100 mm Brownlee Aquapore RP-300 column and a non-linear 0–85% acetonitrile gradient. The purified peptides were subjected to automated Edman degradation using an ABI 470 A Gasphase Sequenator. The program cycles supplied by ABI were modified (one additional coupling step) to increase the repetitive yield. The phenylthiohydantoin derivatives of amino acids were identified by HPLC in an ABI 120A PTH Analyzer with an ABI 900 Data Analysis Module. The HPLC injection vent was equipped with a 100 μsample loop. This enabled the analysis of 83% of the PTH samples thereby improving the sensitivity of the system. Sequence analyses were carried out on 30–50 pmol samples and repetitive yields of 83–93% were obtained.

Three of the resulting peptides separated by reversed phase HPLC were subjected to amino acid analysis and the sequence information used to synthesize short degenerate oligonucleotides. These oligonucleotides were used as primers in PCR (Mullis and Faloona, *Meth. Enzymol.*, 155:335 (1987)) with SKW6.4 cDNA. The primers 5'CCGCTGCAGA(T,C)AC(A,G,C,T)GC(A,G,T,C)GA(A, G)CA(A,G)AA(A, G)GT (upstream primer, sense) and 5'GGGGAATTCTA(A,G,T,C) GC(T,C)TC(T,C)TT(T,C)TT (A,G,TC)CC(AG)TG (downstream primer, antisense) were constructed according to the peptide sequences DTAEQKV (upstream; residues 268 to 275) and HGKKEAY (downstream; residues 285 to 291). Reaction mixtures of 50 μl (10 mM Tris-HCl (pH 8.3), 50 mM KCl, 2.5 mM $MgCl_2$, 0.2 mM each of dGTP, DATP, dCTP, dTTP) contained 50 ng cDNA prepared from polyA$^+$ enriched SKW6.4 RNA (Amersham, cDNA synthesis system plus-kit), 100 pmol of each primer mixture and 1 U *Thermus aguaticus* DNA polymerase (Perkin-Elmer Cetus). 35 cycles (94° C., 1 minute, 48° C., 2 minutes, 72° C., 2 minutes) were performed. The amplified DNA (80bp) was inserted into the vector pBLUESCRIPT-KS (Stratagene, LaJolla, USA) taking advantage of the restriction endonuclease sites present in the 5'-ends of the primers. Transformed bacteria carrying the APO-1-specific insert were identified by colony hybridization probing with oligonucleotide mixtures derived from internal sequences: AA(T,C)TGGCA(T,C)CA(A,G) [TT(A, G);CT(A,G,T,C)]CA(T,C)GG corresponding to NWHQLHG (residues 279 to 286).

An unambiguous cDNA probe completely matching one of the sequenced APO-1 peptides was identified. With this probe, 4 hybridizing plaques were identified out of 1×10⁶ plaques in an SKW6.4 cDNA library. The clone with the longest insert (2.55 kb) was studied further.

A single open reading frame of 1005 nucleotides was found, starting with an ATG (nucleotide 221) that is preceded by an in-frame termination codon TGA (nucleotides 62–64). The sequence flanking the assigned ATG (CAACCATGC) contains seven of nine residues identical to the translation initiation consensus sequence. The open reading frame predicts a protein containing 335 amino acids with features typical of a transmembrane protein. The deduced APO-1 amino acid sequence (single letter code) is shown in the FIGURE. Cysteine residues are marked by an asterisk, the putative leader peptide cleavage site is indicated by an arrow. The putative transmembrane domain is underlined, and potential N-linked glycosylation sites are boxed. Dashed lines represent peptide sequences identified by Edman degradation. Amino acids 1 to 16 are hydrophobic and probably constitute a leader peptide with a putative cleavage point between $A^{16}$ and $A^{17}$. A second hydrophobic region was found at position 172 to 190, flanked on both sides with positively charged residues ($R^{172}$ and $KRK^{193}$) indicative of a transmembrane region.

The N-terminal 155 amino acids contain 18 cysteine residues and two potential N-linked glycosylation sites. The C-terminal 145 amino acids represent the putative intracellular domain of APO-1.

The mature protein has a predicted relative molecular mass of 36 kDa. Data base comparisons of the deduced APO-1 protein sequence revealed significant sequence similarity to the cystein-rich region of the nerve growth factor (NGF) receptor, the B-cell activation antigen CD40, both types of TNF receptors, the rat T cell activation antigen OX40, the deduced protein sequence of the murine cDNA 4-1BB expressed upon T cell activation, and the Shope fibromavirus T2 protein. A lower degree of sequence similarity was also found when the intracellular domains of APO-1, CD40, NGF receptor, and the TNF receptor sequences were compared.

Equivalents

Those skilled in the art will know, or be able to ascertain, using no more than routine experimentation, many equivalents to the specific embodiments of the invention described herein. These and all other equivalents are intended to be encompassed by the following claims.

We claim:

1. A monoclonal antibody or antigen binding fragment thereof which specifically binds to the APO-1 cellular membrane antigen and which induces growth inhibition or cellular apoptosis in APO-1 bearing mammalian cells.

2. A monoclonal antibody of claim 1 which is of the IgG3 isotype.

3. A monoclonal antibody of claim 1, which is murine.

4. A monoclonal antibody of claim 2 which is murine.

5. A monoclonal antibody of claim 1 which is chimeric.

6. A monoclonal antibody of claim 2 which is chimeric.

7. A monoclonal antibody specific for the APO-1 cellular membrane antigen associated with apoptosis.

8. A continuous cell line which produces a monoclonal antibody or antigen binding fragment thereof which specifically binds to the APO-1 cellular membrane antigen and which induces cellular apoptosis in APO-1 bearing mammalian cells.

9. A continuous cell line of claim 8, which is a hybridoma.

10. A composition consisting essentially of an apoptosis inducing amount of a monoclonal antibody in a pharmaceutically acceptable carrier, the antibody characterized by the ability to bind specifically to the APO-1 cellular membrane antigen.

11. The composition of claim 10 wherein the monoclonal antibody is of the IgG3 isotype.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 335 amino acids
        ( B ) TYPE: amino acid
        ( D ) TOPOLOGY: linear ( x i ) SEQUENCE DESCRIPTION: SEQ ID NO:1:

```
Met Leu Gly Ile Trp Thr Leu Leu Pro Leu Val Leu Thr Ser Val Ala
  1               5                  10                  15

Arg Leu Ser Ser Lys Ser Val Asn Ala Gln Val Thr Asp Ile Asn Ser
             20                  25                  30

Lys Gly Leu Glu Leu Arg Lys Thr Val Thr Thr Val Glu Thr Gln Asn
         35                  40                  45

Leu Glu Gly Leu His His Asp Gly Gln Phe Cys His Lys Pro Cys Pro
     50                  55                  60

Pro Gly Glu Arg Lys Ala Arg Asp Cys Thr Val Asn Gly Asp Glu Pro
 65                  70                  75                  80

Asp Cys Val Pro Cys Gln Glu Gly Lys Glu Tyr Thr Asp Lys Ala His
             85                  90                  95

Phe Ser Ser Lys Cys Arg Arg Cys Arg Leu Cys Asp Glu Gly His Gly
            100                 105                 110

Leu Glu Val Glu Ile Asn Cys Thr Arg Thr Gln Asn Thr Lys Cys Arg
            115                 120                 125

Cys Lys Pro Asn Phe Phe Cys Asn Ser Thr Val Cys Glu His Cys Asp
        130                 135                 140

Pro Cys Thr Lys Cys Glu His Gly Ile Ile Lys Glu Cys Thr Leu Thr
145                 150                 155                 160

Ser Asn Thr Lys Cys Lys Glu Glu Gly Ser Arg Ser Asn Leu Gly Trp
                165                 170                 175
```

```
Leu  Cys  Leu  Leu  Leu  Leu  Pro  Ile  Pro  Leu  Ile  Val  Trp  Val  Lys  Arg
          180                      185                     190
Lys  Glu  Val  Gln  Lys  Thr  Cys  Arg  Lys  His  Arg  Lys  Glu  Asn  Gln  Gly
          195                      200                     205
Ser  His  Glu  Ser  Pro  Thr  Leu  Asn  Pro  Glu  Thr  Val  Ala  Ile  Asn  Leu
     210                      215                     220
Ser  Asp  Val  Asp  Leu  Ser  Lys  Tyr  Ile  Thr  Thr  Ile  Ala  Gly  Val  Met
225                      230                     235                          240
Thr  Leu  Ser  Gln  Val  Lys  Gly  Phe  Val  Arg  Lys  Asn  Gly  Val  Asn  Glu
                    245                     250                          255
Ala  Lys  Ile  Asp  Glu  Ile  Lys  Asn  Asp  Asn  Val  Gln  Asp  Thr  Ala  Glu
               260                     265                     270
     Gln  Lys  Val  Gln  Leu  Leu  Arg  Asn  Trp  His  Gln  Leu  His  Gly  Lys  Lys
               275                     280                     285
Glu  Ala  Tyr  Asp  Thr  Leu  Ile  Lys  Asp  Leu  Lys  Lys  Ala  Asn  Leu  Cys
     290                     295                     300
Thr  Leu  Ala  Glu  Lys  Ile  Gln  Thr  Ile  Ile  Leu  Lys  Asp  Ile  Thr  Ser
305                     310                     315                          320
Asp  Ser  Glu  Asn  Ser  Asn  Phe  Arg  Asn  Glu  Ile  Gln  Ser  Leu  Val
                    325                     330                     335
```